US008923954B2

(12) United States Patent
Herman

(10) Patent No.: US 8,923,954 B2
(45) Date of Patent: Dec. 30, 2014

(54) THREE-DIMENSIONAL THERMAL IMAGING FOR THE DETECTION OF SKIN LESIONS AND OTHER NATURAL AND ABNORMAL CONDITIONS

(75) Inventor: Cila Herman, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 161 days.

(21) Appl. No.: 13/809,541

(22) PCT Filed: Jul. 12, 2011

(86) PCT No.: PCT/US2011/043712
§ 371 (c)(1),
(2), (4) Date: Jan. 10, 2013

(87) PCT Pub. No.: WO2012/009359
PCT Pub. Date: Jan. 19, 2012

(65) Prior Publication Data
US 2013/0116573 A1    May 9, 2013

Related U.S. Application Data

(60) Provisional application No. 61/363,466, filed on Jul. 12, 2010.

(51) Int. Cl.
*A61B 6/00* (2006.01)
*A61B 5/00* (2006.01)
*A61B 5/01* (2006.01)

(52) U.S. Cl.
CPC ............... *A61B 5/015* (2013.01); *A61B 5/4836* (2013.01); *A61B 5/7246* (2013.01); *A61B 5/444* (2013.01); *A61B 5/0064* (2013.01); *A61B 5/0075* (2013.01); *A61B 5/441* (2013.01)
USPC ............................ 600/474; 600/473; 382/128

(58) Field of Classification Search
USPC ........................... 600/473–480; 382/128–132
See application file for complete search history.

(56) References Cited

U.S. PATENT DOCUMENTS 6,023,637 A      2/2000   Liu et al.
2004/0236225 A1  11/2004  Murphy et al.
(Continued)

OTHER PUBLICATIONS

Ahuja A S, Prasad K N, hendee W R and Carson P L 1978, Med. Phys. 5(5) 418-21.

(Continued)

*Primary Examiner* — Sanjay Cattungal
(74) *Attorney, Agent, or Firm* — Venable LLP; Henry J. Daley

(57) ABSTRACT

A thermal imaging system includes a data processing system and a geometrical scanning system constructed to communicate with the data processing system. The geometrical scanning system is adapted to scan at least a section of a surface of a subject under observation. The thermal imaging system also includes an infrared imaging system constructed to communicate with the data processing system. The infrared imaging system is adapted to image at least a portion of the section of the surface of the subject under observation. The data processing system is configured to receive data from the geometrical scanning system and to construct a surface map of the section of the surface of the subject under observation and to identify geometrical markers on the surface map based on the data from the geometrical scanning system. The data processing system is also configured to receive data from the infrared imaging system and to construct a thermal map of the portion of the section of the surface, to identify thermal markers on the thermal map based on the data from the infrared imaging system, and to register the thermal map to the surface map based on a correspondence between at least some of the geometrical and thermal markers. The data processor is configured to correct temperatures of the thermal map based on the surface map subsequent to the registering.

31 Claims, 7 Drawing Sheets

(56) References Cited

U.S. PATENT DOCUMENTS

| | | | |
|---|---|---|---|
| 2009/0216130 A1 | 8/2009 | Hirsch et al. | |
| 2010/0041998 A1 | 2/2010 | Postel | |
| 2010/0189313 A1* | 7/2010 | Prokoski | 382/118 |
| 2010/0191124 A1* | 7/2010 | Prokoski | 600/473 |
| 2010/0191541 A1* | 7/2010 | Prokoski | 705/2 |
| 2013/0215928 A1* | 8/2013 | Bellifemine | 374/121 |

OTHER PUBLICATIONS

Amalric, R. et al., 1975, La telethermographie dynamique en dermatologie, Ann. Dermatol. Syphiligr., vol. 102, 157-64.

Amalrich, R. et al., 1984, Value of infrared thermography in the assessment of malignant melanoma of the skin In: Ring EFJ, Phillips B, editors. Recent advances in medical thermography. New York/London: Plenum, vol. 62.

Anbar, M., 1998, Clinical thermal imaging today-shifting from phenomenological thermography to pathophysiologically based thermal imaging, IEEE Eng. Med. Biol. Mag., vol. 17 (4), 25-33.

Anbar, M., 2002, Assessment of physiologic and pathologic radiative heat dissipation using dynamic infrared imaging, Ann. NY Acad. Sci. 972, 111-118.

Anbar et al., 1998, Thermology and facial telethermography. Part I: history and technical review, Dentomaxillofacial Radiology, vol. 27, 61-67, 1998.

Andreassi et al., 2007, Utility and limits of noninvaisve methods in dermatology, Expert Rev. Dermatol., vol. 2, 249-255.9.

Anvari et al., 1995, Phys. Med. Biol. 40(9) 1451-65.

Barnes, R. B., 1968, Diagnostic thermography, App. Opt., vol. 7 (9), 1673-1686.

Boue et al., 2007, Infrared Phys. Tech. 51 13-20.

Bourjat et al., 1975, Diagnosis, follow-up and prognosis of malignant melanomas by thermography, Bibl. Radiol., (6), 115-127.

Brasfield et al., 1964, Thermography in the management of cancer: a preliminary report, Ann. NY. Aca. Sci., vol. 121, 235-247.

Brown S L, Hunt J W and Hill R P 1992, Int. J. Hyperthermia 8(4) 501-14.

Brueschke et al., 1969, Image analysis of medical thermograms, Investigative Radiology, vol. 4, 28-35.

Buzug et al., 2006, Functional infrared imaging for skin-cancer screening, IEEE Eng. Med. Bio. Soc. Conf., 2766-2769.

Cristofolini et al., 1981, Uselessness of thermography for diagnosis and follow-up of cutaneous malignant melanomas, Tumori, vol. 67, 141-143.

Cristofolini et al., 1976, Correlations between thermography and morphology of primary cutaneous malignant melanomas, Acta. Thermogr., vol. 1, 3-11.

Deng Z and Liu J 2005, Proc. 27th IEEE EMBS Ann. Int. Conf. 7525-8.

Di Carlo, A., 1995, Thermography and the possibilities for its applications in clinical and experimental dermatology, Clin. Dermatology, vol. 13, 329-336.

Diakides, N. A., 1998, Infrared imaging: an emerging technology in medicine, IEEE Eng. Med. Bio., vol. 17, 17-18.

Godil, A., 2007, Advanced Human Body and Head Shape Representation and Analysis, Digital Human Modeling, HCII 2007, 92-100.

Gu, J., et al., 1998, A 3D Reconstruction System for Human Body Modeling, Lecture Notes in Computer Science; vol. 1537, 229-241.

Gulyaev, Y. V., Markov, A. G., Koreneva, L. G., Zakharov, P. V., 1995, Dynamical infrared thermography in humans, IEEE Eng. Med. Bio., vol. 14, 766-771.

Hartmann et al., 1981, Telethermography in the diagnostic and management of malignant melanomas, J. Dermatol. Surg. Oncol., vol. 7, 213-218.

He et al., 2008, Comp. Bio. Med. 38 555-62.

Head J F and Elliott r L 2002, IEEE Eng. Med. Bio. 21(6) 80-85.

Head et al., 2000, The important role of infrared imaging in breast cancer, IEEE Eng. Med. Biol. Mag., vol. 19, 52-57.

Helmy et al., 2008, Application of thermography for noninvasive diagnosis of thyroid gland, IEEE Biomedical Eng., vol. 55 (3), 1168-1175.

Hessler et al., 1970, The contribution of thermography to the diagnosis and treatment of malignant melanoma, Schweiz. Med. Wschr., vol. 100(23), 972-975.

Hooshmand et al., 2001, Infrared thermal imaging as a tool in pain management an 11 year study: I, Thermology International, vol. 11, 53-65.

Hundhausen et al., 1979 Eur. J. AppL Physiol. Occup. Physiol. 40(4) 235-44.

Jiang et al., 2005, A perspective on medical infrared imaging, J. Med. Eng. Tech., vol. 29 (6), 257-267.

Jones, B. F., 1998, A reappraisal of the use of infrared thermal image analysis in medicine, IEEE Trans. Med. Imaging, vol. 17 (6), 1019-1027.

Jones et al., 2002, Digital infrared thermal imaging of human skin, IEEE Eng. Med. Bio., vol. 21, 41-48.

Kakuta N, Yokoyama S and Mabuchi K 2002, IEEE Eng. Med. Bio. 21(6) 65-72.

Keyserlingk et al., 2000, Functional infrared imaging of the breast, IEEE Eng. Med. Biol. Mag., vol. 19, 30-41.

Lemons et al., 1987, Am. J. Physiol. 253 128-35.

Leong, I., et al., 2007, Automatic body feature extraction from a marker-less scanned human body, Computer-Aided Design, vol. 39, 568-582.

Luginbuhl, T., et al., 2009, A Model-Based approach for human body reconstruction from 3D scanned data, Lecture Notes in Computer Science, vol. 5496, 332-343.

Merla, A., et al., Jan. 2010, Thermal Imaging of Cutaneous Temperature Modifications in Runners During Graded Exercise, Ann. of Biomedical Eng., vol. 38 (1), 158-163.

Merla et al., 2007, Penile cutaneous temperature in systemic sclerosis: a thermal imaging study, International Journal of Immunopathology and Pharmacology, vol. 20, 139-144.

Mewes et al., 1994, Tomographic measurement and reconstruction techniques, In Optical Measurements—Techniques and Applications, Ed.: F. Mayinger, Springer Verlag, Berlin, 371-424.

Michel et al., 1985, Infrarotthermographie beim malignen melanom, Hautarzt, vol. 36, 83-89.

Mital M and Scott E P 2007, 1 Biomech. Eng. 129 33-9.

Nakagawa et al., 2003, Minim. Invasive Neurosurg. 46(4) 231.

Ng, E. Y. K , 2008, A review of thermography as promising noninvasive detection modality for breast tumor, International Journal of Thermal Sciences, vol. 48, 849-859.

Ng et al., 2009, A review of remote-sensing infrared thermography for indoor mass blind fever screening in containing an epidemic, IEEE Eng. Med. Bio. Mag., vol. 28, 76-83.

Ng et al., 2001, Statistical analysis of healthy and malignant breast thermography, J. Med. Eng. Technol., vol. 25, 253-263.

Nitzan et al., 1989, Clin. Phys. Physiol. Meas. 10 337-41.

Nowakowski, A. Z., 2006, Advances of quantitative IR-thermal imaging in medical diagnostics, Proc. QIRT 2006.

Oliveira, F., et al., 2007, Infrared Imaging Analysis for Thermal Comfort Assessment, IEEE EMBS, 3373-3376.

Ortega, S. S., Garcia Vellado, J. V., 1982, Diagnostico termograpco del melanoma maligno, Actas Dermo-Sif., vol. 73, 89-94.

Otsuka K, Okada S, Hassan M and Togawa T 2002, IEEE Eng. Med. Bio. 21(6) 49-55.

Patel, J. K., et al., 2008, Newer technologies/techniques and tools in the diagnosis of melanoma, Eur. J. Dermatol., vol. 18, 617-631.

Pirtini Cetingul, M. Alani, R. M., and Herman, C., 2010b, Quantitative evaluation of skin lesions using transient thermal imaging, IHTC14-22465, Proceedings of the International Heat Transfer Conference, IHTC14, Aug. 8-13, 2010, Washington, DC, USA.

Pirtini Cetingul, M. Alani, R. M., and Herman, C., 2010c, Detection of skin cancer using skin transient thermal imaging, SBC2010-19193, Proceedings of the ASME 2010 Summer Bioengineering Conference, SBC2010, Jun. 15-19, 2010, Naples, Florida, USA.

Pirtini Cetingul, M. and Herman, C., 2010a, Heat transfer model of skin tissue for the detection of lesions: sensitivity analysis, Phys. Med. Biol., vol. 55, 5933-5951.

(56) References Cited

OTHER PUBLICATIONS

Pirtini Cetingul, M., 2010, Using high resolution infrared imaging to detect melanoma and dysplastic nevi, Ph.D. dissertation, Johns Hopkins University.

Pirtini Cetingul, M., Herman, C., 2008, Identification of subsurface structures from the transient thermal response and surface temperature measurements, Proc. 5th European Thermal-Sciences Conf., May 18-22, 2008, Eindhoven, The Netherlands, ISBN 978-90-386-1274-4.

Pirtini Cetingul, M., Herman, C., 2009a, Identification of skin lesions from the transient thermal response using infrared imaging technique, IEEE 5th Int. Symp. on Biomedical Imaging: From Nano to Macro, May 14-17, 2008, Paris, France, vols. 1-4, 1219-1222.

Pirtini Cetingul, M., Herman, C., 2009b, Transient thermal response of skin tissue, Proc. ASME 2008 Summer Heat Transfer Conf., Aug. 10-14, 2008, Jacksonville, Florida, USA, ASME HT2008-56409, vol. 3, 355-361.

Pirtini Cetingul, M., Herman, C., Alani, R. M., 2009c, Skin imaging with infrared thermography and confocal microscopy, Proc. ASME 2009 Summer Heat Transfer Conf., Jul. 19-23, 2009, San Francisco, California, USA, ASME HT2009-88462.

Psaty, E. L., Halpern, A. C., 2009, Current and emerging technologies in melanoma diagnosis: the state of the art, Clinics in Dermatology, vol. 27, 35-45.

Qi, H., Diakides, N. A., 2007, Infrared imaging in Medicine, CRC Press.

Ring, E. F. J., 1998, Progress in the measurement of human body temperature, IEEE Eng. Med. Bio. Mag., vol. 17, 19-24.

Shrivastava et al., 2005, 1 Heat Trans. 127 179-88.

Stillwagon et al., 1998, Vertebral subluxation correction and its affect on thermographic readings: a description of the advent of the visitherm as applied to chiropractic patient assessment, J. of Vertebral Subluxation Research, vol. 2, 1-4.

Tan et al., 2009, Infrared thermography on ocular surface temperature: A review, Infrared Physics & Technology, 52, 97-108.

Tapernoux et al., 1977, Thermography of malignant melanomas, J. Dermatol. Surg. Oncol., vol. 3, 299-302.

Vainer, G., 2005, FPA-based infrared thermography as applied to the study of cutaneous perspiration and stimulated vascular response in humans, Phys. Med. Biol., vol. 50, 63-94.

Vavilov et al., 2001, Statistical analysis of the human body temperature asymmetry as the basis for detecting pathologies by means of IR thermography, Thermosense XXIII, Proceedings of SPIE, vol. 4360, 482-491.

Wang et al., 2004a, IR imaging of blood circulation of patients with vascular disease, Proc. of SPIE 5405, 115-123.

Wang et al., 2004b, Current technologies for the in vivo diagnosis of cutaneous melanomas, Clin. Dermatology, vol. 22, 217-222.

Wang, C. L., 2005, Parameterization and parametric design of mannequins, Computer-Aided Design, vol. 37, 83-98.

Werghi, N., 2007, Segmentation and Modeling of Full Human Body Shape From 3-D Scan Data: A Survey, IEEE Transactions on Systems, Man, and Cybernetics-Part C: Applications and Reviews, vol. 37 (6), 1122-1134.

Xianwu et al., 2004, Proc. 26th IEEE EMBSs Ann. Int. Conf 873-8.

Zhu et al., 1995, J. Biomech. Eng. 117 64-73.

International Search Report and Written Opinion of PCT/US2011/043712.

\* cited by examiner

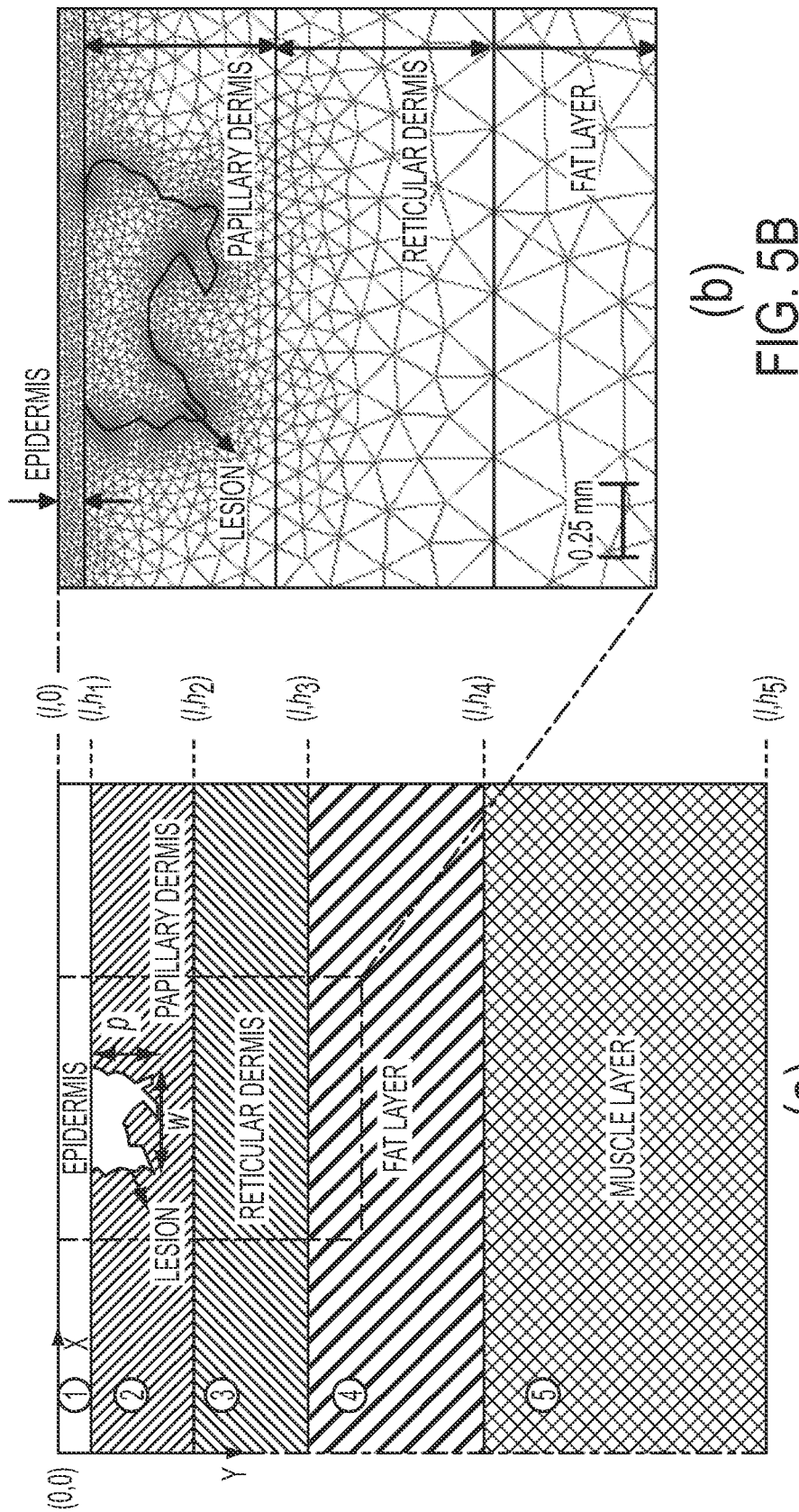

THREE-DIMENSIONAL THERMAL IMAGING FOR THE DETECTION OF SKIN LESIONS AND OTHER NATURAL AND ABNORMAL CONDITIONS

CROSS-REFERENCE OF RELATED APPLICATION

This application claims priority to U.S. Provisional Application No. 61/363,466 filed Jul. 12, 2010, the entire contents of which are hereby incorporated by reference, and is a U.S. national stage application under 35 U.S.C. §371 of PCT/US2011/043712, filed Jul. 12, 2011, the entire contents of which are incorporated herein by reference.

BACKGROUND

1. Field of Invention

The current invention relates to thermal imaging, and more particularly to three-dimensional thermal imaging for the detection of skin lesions and other natural and abnormal conditions.

2. Discussion of Related Art

Thermoregulation is the mechanism that maintains the temperature of the human body within desired boundaries and responds to changes in the ambient and other external and internal variations (caused by disease, physical activity, mechanical or chemical stress and other factors) by controlling the rates of heat generation and heat loss. Thermoregulation is one aspect of homeostasis, a dynamic state of stability between the internal and external environments. The temperature distribution in the human body depends not only on physical parameters, but also on the physiology associated with the homeostatic and metabolic processes as well as the structure and dynamics of the tissue, vascular and nervous systems. There is a large body of evidence that disease or deviation from normal functioning are accompanied by changes in temperature of the body, which again affect the temperature of the skin (Jones, 1998, Anbar, 1998). The behavior of tumors differs from that of healthy tissue in terms of heat generation, because of processes such as inflammation, increase in metabolic rate, interstitial hypertension, abnormal vessel morphology and lack of response to homeostatic signals (Ring, 1998, Anbar, 2002). Clearly, accurate data about the temperature of the human body and skin can provide a wealth of information on the processes responsible for heat generation and thermoregulation, in particular the deviation from normal conditions, often caused by disease.

Infrared thermography is a non-invasive tool that allows the measurement of the spatial and temporal variations of temperature associated with the IR radiation emitted by the object under study, which is the human body in embodiments of the current invention. The emitted radiation and the skin surface temperature carry a wealth of information about different processes within the human body. The advances in IR cameras, computers and imaging techniques led to increasing interest in infrared thermography in medical diagnostics and other biomedical and engineering applications (Gulyaev et al. 1995, Jones and Plassmann, 2002, Vaviov et al. 2001). Past applications of infrared thermography focused on the imaging of relatively small areas of the body, and the imaging was often qualitative, with a low resolution.

Cancer is the second leading cause of death in the United States as well as worldwide. New techniques to detect cancer at an early stage are being explored in numerous laboratories and research centers all over the world, and noninvasive diagnostic tools are of particular interest. Each technique offers unique advantages and disadvantages, many of which pose a compromise between effectiveness and accuracy versus cost considerations and invasiveness. While the precision of MRI is unmatched in detecting internal lesions, infrared imaging has been proven useful in the study of skin and subsurface tumors such as breast cancer, skin cancers (melanoma), as well as arteriosclerosis, peripheral vascular disease, burn injuries, infections, Lyme disease lesions, pressure ulcers, contamination with chemicals (in chemical warfare and homeland security), athletic performance, etc (Ng, 2008, Carlo, 1995, Merla et al. 2007, Helmy et al. 2008, Tan et al. 2009, Vainer, 2005, Oliveira et al. 2007, Wang et al. 2004, Merla et al. 2010).

3d Topographic Mapping of the Human Body.

Accurate 3d imaging and reconstruction of the human body in general, or that of a specific human subject, is of interest in numerous engineering (military and aerospace—virtual reality simulations; entertainment—computer games, movies, animation; industrial—development of equipment, protective clothing, etc.) and medical applications (diagnostics, rehabilitation, prosthetics, analysis and enhancement of athletic performance). Spatial accuracy is of primary concern in medical diagnostics applications when 3D data is captured for a real human body.

There are two basic categories of technologies employed in human body imaging/scanning: laser-based technologies and Moiré fringing. Both technologies are optical and they do not require direct contact. In the laser-based technology, a laser beam is projected from eight laser diodes onto the body, scanning it from top to bottom. The laser stripe deformed by the body surface is captured and recorded by different cameras strategically positioned around the body. The recorded data represent the location of the laser stripe with respect to the camera reference. A software program combines the data from each camera using triangulation and produces a set of 3D data points representing the body surface. The duration of the scan is around 17 s. The number of 3d data points generated is of the order of 100,000 points (Werghi, 2007).

Moiré imaging techniques have been used to measure surface topography in a variety of medical and engineering applications. Typically the surface area analyzed is smaller than what is required in full-body imaging. There is a significant body of literature that analyzes the factors that affect the formation of the fringes, such as gratings, light sources of finite dimensions, intensity distribution of the light source, viewing aperture function, lateral displacement of the source relative to the viewing axis, the viewing distance, grating spacing and grating ratio, etc.

Moiré fringing technology employs a Moiré-based light projection system, also known as phase measuring profilometry. In this system, a white light source is used to project contour patterns (sinusoidal fringes) on the body surface and these patterns, distorted by curves in the body surface, are detected by a set of cameras arranged around the subject. The superimposed deformed patterns generated in this way interact with other patterns used as reference points and form fringes that describe the body surface contours. Subsequently, the data obtained from the separate fringes are combined into a single reference, yielding a cloud in which the 3D data points represent the body surface. Scan time in this technology is around 6 s. The average data density of scanner is 800,000 points (Werghi, 2007).

Human body scanning can provide clouds of more than 200,000 points representing the 3D human body. However, getting an accurate model from scanned data is not a straightforward task. The three main areas of research in managing scanned data are human body modeling, body landmark detection, and segmentation (Werghi, 2007). Segmentation provides a labeling of the body that can be used to reduce the search space for body landmarks. In dynamic human body modeling, segmentation has contributed to solving problems arising in data registration. By identifying body parts in different poses, it permits important correspondences between the related data sets. There have been many research efforts put into these post-processing of scanned data. Wang (2005) developed an algorithm to extract key features on the human body, and then built a set of parametric surfaces to represent the scanned subject. Luginbuhlt et al. 2009 used a generic model which is segmented and points are organized in slices. They adapted the sizes of each body limb and then fitted each slice to the data. Leong et al. 2007 employed image processing and computational geometry techniques to identify, automatically, body features from a markerless scanned body.

Gu et al. (1998) developed hardware and software to model the human body using laser-based technology. The hardware consists of the equipment-supporting framework, cameras and lenses, lighting arrangement and sensors for synchronization. 12-13 cameras are used in the system. Six views are used to cover the 360° circular reconstruction space. An additional view is needed for the frontal image to obtain better information of the chest, the armpit and the crotch. The target object to be imaged is up to 2 m tall, so two cameras are used for each viewpoint, in order for the full length of the object to be imaged. The imaging software consists of five modules: camera calibration, image capturing, image processing, model reconstruction and virtual measurement modules. During the imaging process, the human subject is required to wear tight clothing and stand in the center of the imaging space so that the body can be visible to all of the cameras. To obtain clear contours of the body, the subject is asked to open his or her arms and also to keep his or her two legs slightly apart.

Another study of particular interest is the one by Godil (2007). This author relied on the CAESAR anthropometric database (a database of approximately 5000 3d scans of human bodies). They developed two representations based on human body shape: (i) a descriptor vector based on lengths, mostly between single large bones (3D body description vector of fifteen distances, such as wrist to elbow, elbow to shoulder, hip to knee, etc.) as well as (ii) three silhouettes of the human body are created by rendering the human body from the front, side and top. In addition to the human body, they developed two representations for the human head.

IR Imaging: Medical Applications and Potential for Full Body Scanning.

Measuring and visualizing the local skin temperature is a useful approach to diagnose the signs of disease. IR imaging is a non-invasive method that measures spatial variations in skin temperature that can be caused by a variety of conditions, e.g., contusions, fractures, burns, carcinomas, lymphomas, dermatological diseases, rheumatoid arthritis, diabetes mellitus, bacterial infections, etc. These conditions are commonly associated with regional vasodilation, hyperthermia, hyperperfusion, hypermetabolism, and hypervascularization, that manifest as a heat source associated with higher temperature.

IR imaging is especially suitable for diagnosing peripheral vascular disorders, inflammatory disease, tumors, local metabolic disorders, and body temperature abnormalities. So far IR systems have been used to diagnose breast cancer (Ng, 2008), rheumatism (Ring, 1998), skin lesions (Di Carlo, 1995), fever (Ng and Acharya 2008), impotence (Merla et al. 2007), thyroid gland disease (Helmy et al. 2008) and eye diseases (Tan et al. 2009). IR imaging also assists in decision making in open-heart surgery due to its ability to provide real-time information (Ruddock, 2008). It was applied for the management of neuropathic pain (Hooshmand et al. 2001), the assessment of patient response to chiropractic care by measuring the temperature gradients in clinical setting (Stiliwagon, 1998), the evaluation of cerebral thermoregulation (facial thermography) (Oliveira et al. 2007) and sweat glands (Vainer, 2005). In addition to considering abnormalities, IR imaging is also used to visualize the human body anterior cutaneous temperature variations in well-trained runners and to quantitatively evaluate the specific cutaneous whole body thermal adaptations that occur during and after graded physical activity (Merla et al. 2010).

In IR imaging, diagnosis is often made by comparing temperature asymmetry between healthy and diseased regions of the body: a change in temperature is considered to be a sign of abnormal functioning (Vaviov et al. 2001). Anbar (1998) found that the diagnosis of neurological, musculoskeletal or other tissue abnormalities by IR imaging is based on pathological changes in the spatial distribution of temperature over the skin surface as well as pathological changes in the dynamic behavior, i.e., warming, cooling, or periodic modulation of temperature of a given subarea of the skin.

In order to use IR imaging for clinical diagnosis, it is necessary to determine the location of the abnormal thermal areas as well as the degree of change in body-surface temperature. It is useful to cross-reference the resulting IR images with visual images of the patient and then the segment region of interest in IR images to locate the subregions of interest (Schaefer et al. 2006, Yoon et al. 2006). Mabuchi et al. 1998 divided the body surface into two symmetrical sections: the healthy side and the affected side. Each part was then further divided into the same number of symmetrical trapezoidal or triangular pairs. Ring et al. 2004 specified a total of 27 views of the body and defined 87 regions of interest (ROI) in terms of the shape of the area for each view. The mean temperature and standard deviations of the temperatures within the ROIs and along the cross-sections are compared in the diagnostic imaging process.

IR Imaging in the Diagnosis of Breast Cancer.

Despite advances in treatment that have reduced mortality, breast cancer remains the second leading cause of cancer deaths in women today (Kennedy et al. 2009). Clinical breast exam and mammography are the two most widely used tools to screen for breast cancer. In addition to these methods, IR imagining has been approved by the FDA since 1982 as a screening tool for breast cancer. IR imaging was first introduced as a screening tool in 1956, after the observation of asymmetric hot spots and vascularity in infrared images of breast cancer patients. When a malignant tumor develops in a breast, it will cause prominent localized increase of skin surface temperature due to the high metabolic activity and blood perfusion of the tumor (Jones 1998). This localized temperature difference shows up as a spot or vascular pattern in a breast infrared image that is called a heat pattern. Breast cancer can be detected through the visual analysis of thermal patterns by physicians (Jones, 1998, Keyserlingk et al. 2000, Head et al. 2000, Ng et al. 2001).

Feig et al. (1977) compared the sensitivity of steady-state (active) IR imaging to other methods of breast cancer detection. The result of this study showed that active IR imaging has a sensitivity of only 39% and a specificity of 82%. The major difficulty in the interpretation of breast IR imaging is the complexity of the vascular patterns (false negatives and false positives) and it is reported that a high thermal gradient for a hot spot over a tumor was the most important factor to differentiate a malignancy from a benign condition (Jones 1998, Keyserlingk et al. 2000, Head et al. 2000, Ng et al. 2001). Therefore, in order to better differentiate breast cancer from benign breast disease, IR imaging should be done during thermal recovery (dynamic mapping). Since then, many attempts have been made to diagnose breast cancer with dynamic IR imaging and several methods of evaluation have been proposed in order to improve its diagnostic value (Jones, 1998, Keyserlingk et al. 2000, Head et al. 2000, Ng et al. 2001, Amalu, 2004, Tang et al. 2008, Arora et al. 2008, Ohashi and Uchida 2000). When a breast is exposed to cold stress, the vascular pattern disappears, and after the stress is removed, the pattern gradually recovers. This phenomenon of thermal recovery can be visualized by sequential IR imaging or by digital subtraction IR imaging (Ohashi et al. 1994). Keyserlingk et al. (1998) found the sensitivity of IR imaging to be 83%. The combination of mammography and IR imaging increased the sensitivity to 95%. In light of developments in computer technology and the maturing of the thermographic industry, additional improvements are required to develop this technology to provide effective noninvasive early detection of breast cancer (Kennedy et al. 2009).

Melanoma.

Melanoma incidence is increasing at one of the fastest rates for all cancers in the United States with a current lifetime risk of 1 in 58. Over 60,000 patients are expected to be diagnosed with melanoma in the US with more than 8,000 deaths in 2008. The reported 1-year survival rates for patients with advanced melanoma range from 40% to 60%, and systemic agents are not currently available to significantly extend the lifespan of patients with advanced disease. These statistics stress the need to detect melanomas at their earliest stages for chances of optimal cure and to identify patients with high-risk primary disease for the initiation of early prophylactic treatment.

The increased availability of thermal imaging cameras has led to a growing interest in the application of infrared imaging techniques to the detection and identification of subsurface structures both in engineering and in living systems. Infrared (IR) imaging is a non-contact sensing method concerned with the measurement of electromagnetic radiation in the infrared region of the spectrum (750 nm-100 µm). Radiation emitted by a surface at a given temperature is called spectral radiance and is defined by the Planck's distribution for the idealized case of a blackbody. Infrared cameras detect this radiation and the surface temperature distribution can be recovered after post-processing the sensor information and appropriate calibration. Since the surface temperature distribution depends on the properties of subsurface structures and regions, infrared imaging can be used to detect and identify subsurface structures by analyzing the differences in the thermal response of an undisturbed region such as healthy skin and a near-surface structure of different properties such as a skin lesion.

Infrared imaging can be performed either passively or actively (dynamically). Passive infrared imaging involves, in its simples form, the visualization of the emitted radiation in the infrared region of the electromagnetic spectrum, for example night vision goggles, and, in more advanced imaging applications, measuring (after post processing of the information acquired by the sensor and appropriate calibration) temperature variations of structures whose temperature naturally differs from ambient temperature or varies locally due to internal heat sources. Active infrared imaging involves introducing external forcing such as heating or cooling to induce and/or enhance relevant thermal contrasts observed on the surface. The latter technique is based on the following principle: when a surface is heated or cooled, variations in the thermal properties of a structure located underneath the surface result in identifiable temperature contours on the surface itself, differing from those present in the steady-state situation during passive imaging as well as from the surrounding regions. These contours are characteristic of the thermal properties of the base structure and subsurface perturbations, and can, when combined with a suitable model, provide information regarding the shape and depth of the perturbation (a lesion in our study). Thus, the dynamic thermal response of the structure obtained using the active imaging provides additional information useful in the identification of the perturbation when compared to information obtained by passive imaging.

Infrared imaging has been successfully applied in various problems in engineering and medicine. Recent improvements in infrared sensor and computer technology led to the resurgence of infrared imaging in medicine. In particular, describing the thermal response of chemically and metabolically active multilayered samples constitutes an important problem. For instance, thermal modeling of temperature distributions linked to large blood vessels has received a great deal of attention in the research community (Hundhausen, E and Theves B 1979 *Eur. J. Appl. Physiol. Occup. Physiol.* 40(4) 235-44; Lemons D E, Chien S, Crawshaw L I, Weinbaum S and Jiji L M 1987, *Am. J. Physiol.* 253 128-35; Nitzan M, Mahler Y, Roberts J, Khan O, Gluck E, Roberts V C and Baum M 1989, *Clin. Phys. Physiol. Meas.* 10 337-41; Zhu L and Weinbaum S 1995, *J. Biomech. Eng.* 117 64-73; Nakagawa A, T. Hirano, Uenohara H, Sato M, Kusaka Y, Shirane R, Takayama K and Yoshimoto T 2003, *Minim. Invasive Neurosurg.* 46(4) 231). Shrivastava et al (Shrivastava D, McKay B and Roemer R B 2005, *J. Heat Trans.* 127 179-88) derived an analytical model describing the tissue temperature distribution in unheated/heated, finite, noninsulated tissue with a pair of vessels to quantify the vessel-vessel and vessel-tissue heat transfer rate. He et al (He Y, Liu H, Himeno R, Sunaga J, Kakusho H and Yokota H 2008, *Comp. Bio. Med.* 38 555-62) developed a FEM model based on the heat transport in porous media to simulate blood flow in large vessels and living tissue. Boue et al (Boue C, Cassagne F, Massoud C and Fournier D 2007, *Infrared Phys. Tech.* 51 13-20) analyzed the infrared images to extract the radius, depth and the blood flow velocity in a vein.

In order to understand the physics of IR imaging in the analysis of lesions, first, it is worth recalling that the chemical reactions, blood transport, perfusion and metabolic processes that affect local temperature response in normal tissue are under both global and local control (Gulyaev Y V Markov A G Koreneva L G and Zakharov P V 1995, *IEEE Eng. Med. Bio.* 14(6) 766-71; Jones B F and Plassmann P 2002, *IEEE Eng. Med. Bio.* 21(6) 41-48; Otsuka K, Okada S, Hassan M and Togawa T 2002, *IEEE Eng. Med. Bio.* 21(6) 49-55; Kakuta N, Yokoyama S and Mabuchi K 2002, *IEEE Eng. Med. Bio.* 21(6) 65-72). When a cancerous lesion develops, affected tissue has escaped from the control of the various feedback systems and mechanisms present in healthy tissue, leading to such abnormal processes as cell proliferation, disordered spatial organization and excess metabolism i.e. heat generation (Brown S L, Hunt J W and Hill R P 1992, *Int. J. Hyperthermia* 8(4) 501-14; Jones B F 1998, *IEEE Trans. Med. Imaging* 17(6) 1019-27). Examples of such a response include Kaposi Sarcoma, melanoma, neuroblastoma, wine stain birthmarks, breast cancer, etc. (Ahuja A S, Prasad K N, Hendee W R and Carson P L 1978, *Med. Phys.* 5(5) 418-21; Anvari B, Tanenbaum B S, Milner T E, Kimel S, Svaasand L O and Nelson J S 1995, *Phys. Med. Biol.* 40(9) 1451-65, Head J F and Elliott R L 2002, *IEEE Eng. Med. Bio.* 21(6) 80-85;

Xianwu T, Haishu D, Guangzhi W and Zhongqi L 2004, *Proc. 26th IEEE EMBS Ann. Int. Conf.* 873-8; Deng Z and Liu J 2005, *Proc. 27th IEEE EMBS Ann. Int. Conf.* 7525-8; Buzug T M, Schumann S, Pfaffmann L, Reinhold U and Ruhlmann J 2006, *Proc. 28th IEEE EMBS Ann. Int. Conf.* 2766; Mital M and Scott E P 2007, *J. Biomech. Eng.* 129 33-9).

Although there has been significant interest in IR based systems for medical applications, they have remained of limited usefulness. Therefore, there a need in the art for improved high-resolution thermal imaging systems.

SUMMARY

A thermal imaging system according to an embodiment of the current invention includes a data processing system and a geometrical scanning system constructed to communicate with the data processing system. The geometrical scanning system is adapted to scan at least a section of a surface of a subject under observation. The thermal imaging system also includes an infrared imaging system constructed to communicate with the data processing system. The infrared imaging system is adapted to image at least a portion of the section of the surface of the subject under observation. The data processing system is configured to receive data from the geometrical scanning system and to construct a surface map of the section of the surface of the subject under observation and to identify geometrical markers on the surface map based on the data from the geometrical scanning system. The data processing system is also configured to receive data from the infrared imaging system and to construct a thermal map of the portion of the section of the surface, to identify thermal markers on the thermal map based on the data from the infrared imaging system, and to register the thermal map to the surface map based on a correspondence between at least some of the geometrical and thermal markers. The data processor is configured to correct temperatures of the thermal map based on the surface map subsequent to the registering.

A method of processing thermal imaging data according to an embodiment of the current invention includes receiving data from a geometrical scanning system taken from a scan of at least a section of a surface of a subject under observation, receiving data from an infrared imaging system for at least a portion of the section of the surface, constructing a surface map of the section of the surface of the subject under observation and identifying geometrical markers on the surface map based on the data from the geometrical scanning system, constructing a thermal map of the portion of the section of the surface, identifying thermal markers on the thermal map based on the data from the infrared imaging system, registering the thermal map to the surface map based on a correspondence between at least some of the geometrical and thermal markers, and correcting temperatures of the thermal map based on the surface map subsequent to the registering the thermal map to the surface map.

A computer readable medium according to an embodiment of the current invention includes software, which software, when executed by a computer, causes the computer to receive data from a geometrical scanning system taken from a scan of at least a section of a surface of a subject under observation, receive data from an infrared imaging system for at least a portion of the section of the surface, construct a surface map of the section of the surface of the subject under observation and identify geometrical markers on the surface map based on the data from the geometrical scanning system, construct a thermal map of the portion of the section of the surface, identify thermal markers on the thermal map based on the data from the infrared imaging system, register the thermal map to the surface map based on a correspondence between at least some of the geometrical and thermal markers, and correct temperatures of the thermal map based on the surface map subsequent to the registering the thermal map to the surface map.

BRIEF DESCRIPTION OF THE DRAWINGS

Further objectives and advantages will become apparent from a consideration of the description, drawings, and examples.

In FIG. 4, the grayscale information a) as delivered by the camera (top row of images) b) and corresponding reconstructed temperature fields color coded using false colors are shown. The first two pairs of images (grayscale and color-coded) were recorded after applying FP1, FP2 (FP—focal pressure), and LS (line scratch). The remaining three pairs of images show different time instants during the recovery phase.

FIGS. 5A and 5B illustrate a) cross-sectional view of skin layers and lesion with coordinates system, and b) magnified area of lesion showing the finite mesh model according to an embodiment of the current invention.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Some embodiments of the current invention are directed to a high-resolution, high-accuracy imaging system to measure the skin temperature of the human body, or portions thereof, by combining accurate three-dimensional mapping and thermal imaging. Some embodiments further include a three-dimensional computational thermal model of the human body, for example by coupling simplified thermal models of body parts (head, torso and limbs) to a more accurate thermal model of the skin. The model can utilize the geometrical information obtained from the three-dimensional mapping and the temperature data obtained by the IR imaging system. The information obtained from coupled imaging and modeling can provide an aid for the diagnosis of disease and the evaluation and understanding of the functioning of the body in response to external or internal stress in a variety of situations of interest in biomedical engineering and medicine, for example.

Figure 1A:
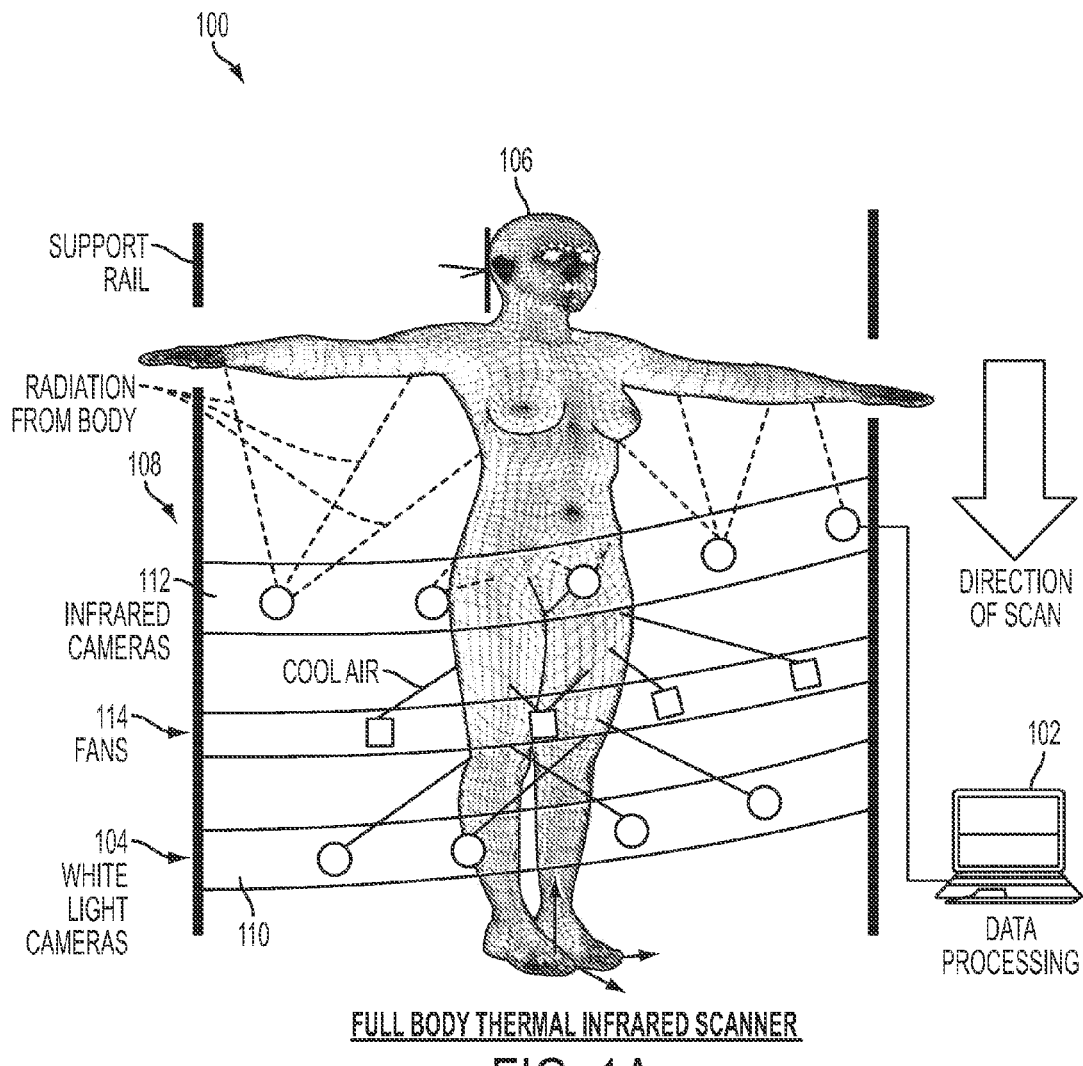
FIGS. 1A and 1B are schematic illustrations of front and top views, respectively, of a thermal imaging system according to an embodiment of the current invention.
Figure 1B:
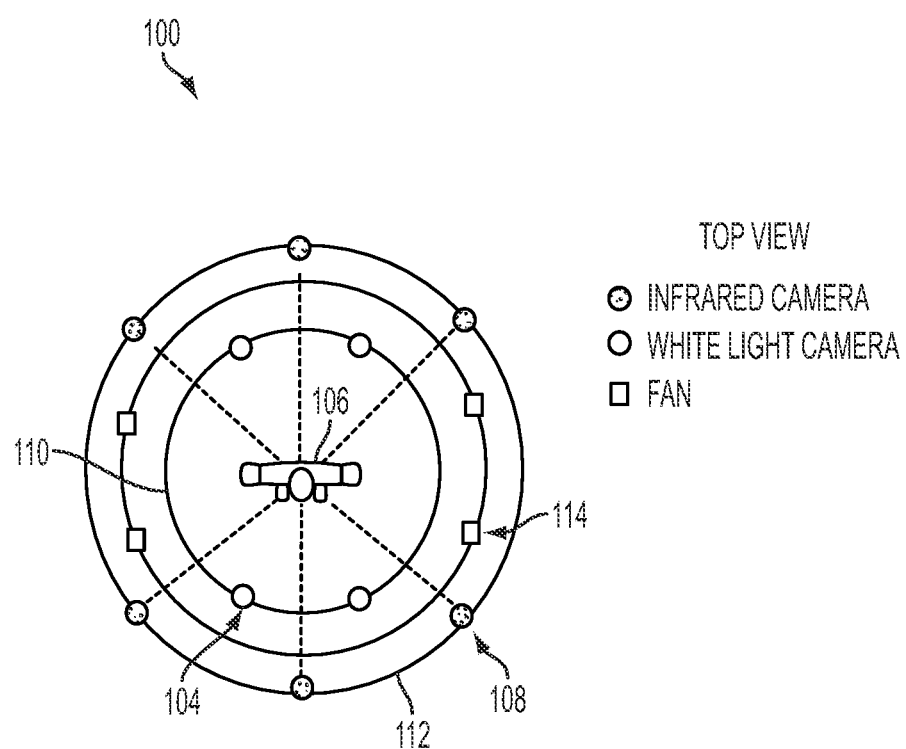

FIG. 1A is a schematic illustration (front view) of a thermal imaging system 100 according to an embodiment of the current invention. (FIG. 1B shows the corresponding top view.) The thermal imaging system 100 includes a data processing system 102, a geometrical scanning system 104 constructed to communicate with the data processing system 102. The geometrical scanning system 104 is adapted to scan at least a section of a surface of a subject 106 under observation. The thermal imaging system 100 also includes an infrared imaging system 108 constructed to communicate with the data processing system 102. The infrared imaging system 108 is adapted to image at least a portion of the section of the surface of the subject 106 under observation. The data processing system 102 is configured to receive data from the geometrical scanning system 104 and to construct a surface map of the section of the surface of the subject 106 under observation and to identify geometrical markers on the surface map based on the data from the geometrical scanning system. The data processing system 102 is also configured to receive data from the infrared imaging system 108 and to construct a thermal map of the portion of the section of the surface of the surface of the subject 106 under observation, to identify thermal markers on the thermal map based on the data from the infrared imaging system, and to register the thermal map to the surface map based on a correspondence between at least some of the geometrical and thermal markers. The data processing system 102 is also configured to correct temperatures of the thermal map based on the surface map subsequent to the registering.

The geometrical scanning system 104 can include one or more white light cameras, for example. In the embodiment of FIG. 1, four white light cameras are illustrated in the drawing. However, the concepts of the current invention are not limited to this example. For example, additional cameras can be provided to extend entirely around the subject 106 such that a full body scan can be made with each scan. Other embodiments can include different numbers of cameras, as well as other types of optical systems, such as LED and/or laser illuminators. The geometrical scanning system 104 includes a scanning assembly 110 on which the plurality of white light cameras are attached. In this embodiment, the scanning assembly 110 can be scanned, for example, starting at the subject's feet and completing a scan at the top of the subject's head. Such an arrangement for the geometrical scanning system 104 can be useful to reduce the number of cameras that are needed to generate a surface map, especially for whole-body or half body applications. The general concepts of the current invention are not limited to this particular type of geometrical scanning system 104. For example, a scanning system with a sufficient number of white light cameras to cover the whole body, or portion of the body of interest, could be "scanned" electronically. In some applications, the thermal imaging system 100 can be a whole-body scanner or a half-body scanner (e.g., front half or back half), for example.

However, other embodiments of the thermal imaging system 100 can be partial body scanners. For example, without limitation, the thermal imaging system 100 can be a dedicated thermal imaging system to assists with screening for breast cancer.

The infrared imaging system 108 can, similar to the geometrical scanner, include one or more infrared cameras. They can similarly be mounted on a scanning assembly 112, as illustrated in FIG. 1. The scanning assembly 112 can be attached to, integral with or separate from the scanning assembly 110, for example. Similar to the geometrical scanner 104, the IR imaging system could be a plurality of fixed IR cameras in some embodiments.

In order to achieve adequate resolution for medical applications, a resolution of at least 0.25 mm×0.25 mm for both the geometrical scanning system and infrared imaging system 108 is provided. Temperature resolution (sensitivity) of at least 0.025° K is provided.

The thermal imaging system 100 also includes a thermal stimulation system 114 arranged to thermally stimulate at least a portion of the section of the surface of the subject 106 under observation. In this example, the thermal stimulation system 114 includes a plurality of fans that cool regions of the subject 106 that are under observation. Other arrangements of fans or other cooling and/or heating devices can be included in some embodiments of the current invention.

In some embodiments of the thermal imaging system 100, the data processing system 102 is also configured to receive data from the infrared imaging system 108 at a plurality of times, including at least one time prior to and at least one time subsequent to a thermal stimulation from the thermal stimulation system 114. The data processing system 102 is configured to construct a plurality of thermal maps of the portion of the section of the surface corresponding to each of the plurality of times and to register each of the plurality of thermal maps to a corresponding surface map. The data processor is also configured to correct temperatures of each of the plurality of thermal maps based on the corresponding surface map subsequent to the registering. In some embodiments, once the surface map is generated, the same surface map can be used for registering the plurality of thermal maps. This can be useful for cases in which there is little significant change in the surface map of the subject over the time period between scans. In other embodiments, changes in the surface map may be simple changes such as small translations and/or rotations of the subject 106, for example. In some cases, it can be sufficient to treat the translations and rotations as rigid body motion and simply correct the surface map for the rigid body motion. In some embodiments, indicia and/or sensors can be included to track motion of the subject 106. In some embodiments, surface maps can be generated for multiple scan, or even for every scan, as desired.

In some embodiments of the current invention, the thermal imaging system 100, the data processor 102 is further configured to process the plurality of thermal maps to identify regions having abnormalities in thermal response. In some embodiments, time dependence of thermal responses can be included in identifying the regions having abnormalities in thermal response. In some embodiments, the data processor 102 can be further configured to process the plurality of thermal maps using a thermodynamic model to identify regions having abnormalities in thermal response. In some embodiments, the thermodynamic model can include a three-dimensional model of a section of the body of the subject 106. In some embodiments, the thermodynamic model instead, or additionally, includes a detailed thermodynamic model of skin layers that include an abnormality. The abnormality in a detailed skin model can be melanoma, for example.

Some embodiments of the current invention are directed to methods of processing thermal imaging data. For example, some methods can perform, but are not limited to, the following:
1. Take sets of white light images.
2. Map white light images onto 3D space.
3. Take sets of reference IR images.
4. Align IR images with white light images using markers.
5. Map IR information onto 3D space.
6. Apply thermal stimulation.
7. Record IR movie of thermal recovery as a function of time.
8. Map thermal recovery onto 3D space with the aid of thermal markers.
9. Apply motion tracking to compensate for involuntary motion.
10. Locate lesions in IR recovery image by mapping white light location onto thermal recovery locations.
11. Compare thermal responses of healthy tissue and lesions.
12. Move assembly and apply imaging to the next region of the body.

Some embodiments of the invention can allow for earlier detection of skin cancers at their most curable point, thus reducing the mortality associated with more invasive, later stage melanomas, for example. The general concepts of the current invention are not limited to only to the early identification of melanoma. For example, other abnormalities can include: large pigmented lesions such as Giant Congenital Nevi, Non-melanoma skin cancers (these may include Basal Cell Carcinoma (BCC), Squamous Cell Carcinoma (SCC), Cutaneous Lymphomas, Merkel Cell Carcinomas, Histiocytosis, Leukemia Cutus, other primary or secondary cutaneous malignancies, hamartomatous lesions with cancer risk (e.g. Nevus Sebaceous, etc), cutaneous vascular lesions (hemangiomas, port-wine stain lesions, and other vascular abnormalities); primary inflammatory/autoimmune diseases of the skin (psoriasis, eczematous dermatitis, seborrheic dermatitis, lichenoid dermatitis, pityriasis, pyoderma gangrenosum, bullous pemphigoid, pemphigus vulgaris, other autoimmune disorders of skin), secondary inflammatory diseases of the skin (autoimmune lupus, scleroderma, dermatomyositis, Steven's-Johnson syndrome, erythema multiforme, toxic epidermal necrolysis, staph scalded skin syndrome, pyoderma gangrenosum, urticaria, vasculitis, drug hypersensitivity reactions, etc), primary and/or secondary infectious disease (human papillomavirus (HPV)/warts, herpes simplex, varicella zoster, molluscum contagiosum, folliculitis, acne vulgaris, bacterial/viral/fungal infections, etc), cutaneous lesions associated with infectious agents (acne vulgaris, HPV-associated infection (warts), mollluscum contagiosum, folliculitis, and other bacterial infections); grade the amount of "skin aging" changes including skin thinning and subtle skin textural changes; pressure ulcers; burn injuries; grade quantitatively infected skin/wounds; grade wound healing; grade the success of antibiotic or topical treatments.

The current inventor conducted prior work related to dynamic IR processes in localized systems in which the region was sufficient small that the effects of surface curvature, etc could be ignored (see, e.g., international application PCT/US2009/003319, assigned to the current assignee as the current application; and Herman et al. 2007; the entire contents of which are incorporated herein by reference). We proposed that malignant (pigmented) lesions with increased proliferative potential generate quantifiable amounts of heat (Pirtini Cetingul and Herman 2008, 2009a,b; the entire contents of which are incorporated herein by reference) and possess an ability to reheat differently, more quickly, (after a cooling stress is applied to the lesion and its surroundings and then removed) than surrounding normal skin, thereby creating a marker of cancerous lesions, such as melanoma (vs. non-proliferative nevi), as shown in FIGS. 2A-2K and 3A-3E.

Figures 3A, 3B, 3C, 3D, 3E:
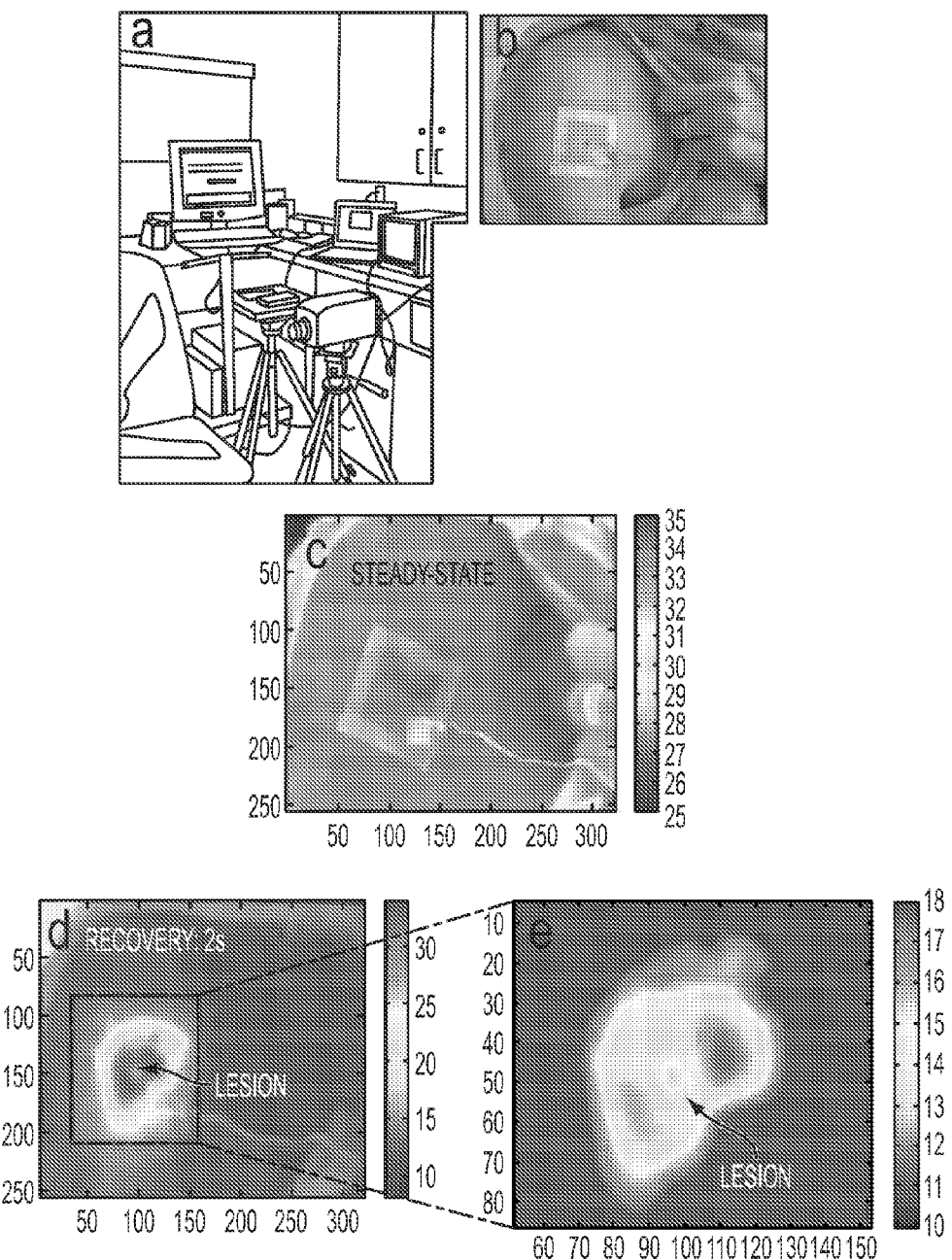
FIGS. 3A-3E show a) the infrared imaging system HRIS in the clinical trial room, b) photograph of the larger body surface area with a cluster of pigmented lesions and the template frame applied for imaging, c) reference infrared image of the region at ambient temperature, d) the same area after cooling and e) magnified section of the melanoma lesion and surroundings that can be used with embodiments of the current invention.

We have recently developed an IR imaging system that allows for accurate measurement of temperature variations of the skin (Pirtini Cetingul and Herman 2008, 2009a,b,c), shown in FIGS. 3A-3E. Embodiments of the current invention include High-Resolution Infrared Scanning (HRIS) technology in order to develop an accurate, simple, non-invasive, quantitative (objective) screening and diagnostic tool to distinguish benign from malignant pigmented lesions and assess melanoma risk. Some embodiments of the current invention can provide (i) rapid, total cutaneous imaging through a total body scanning system as well as (ii) the assessment of the malignant potential of the individual lesion. FIG. 3A shows components of the infrared imaging system used in this case. The infrared camera operates in the 3-5 micrometer band and another camera captures information in the visible wavelength range.

Our theoretical and experimental results show a correlation between the transient surface temperature signature and the heat generation/metabolic activity level, size, shape and location of subsurface structures, such as melanoma or other cancerous or non-cancerous lesions. These data were reported in several publications (Pirtini Cetingul and Herman 2008, 2009a,b, 2010, the entire contents of which are incorporated herein by reference). In order to relate the transient surface temperature signature to different characteristics of subsurface structures, accurate computational models were developed. The accuracy of these models was first verified experimentally on a skin phantom experiment in the Heat Transfer Lab of JHU. Clinical trials (Johns Hopkins Medical Institutions IRB, Mar. 30, 2009, protocol: NA_00016040, Using High Resolution Functional Infrared Imaging to Detect Melanoma and Dysplastic Nevi) with the HRIS imaging system began in the fall of 2009 in the Pigmented Lesion and Melanoma Clinic at JHU and in vivo data became available recently. Key results relevant for the proposed study are summarized below.

Sample images and results demonstrating the feasibility of the our approach are displayed in FIGS. 2A-2K, contrasting images and data obtained for a benign pigmented lesion (left hand side column, FIGS. 2A, 2B, 2F, 2H, 2J) and a malignant melanoma lesion (right, FIG. 2C-2E, 2G, 2I, 2K). Clinical assessment of the benign lesion characterized this upper midback lesion as a benign congenital nevus with compound features. Prior to the biopsy, clinical assessment characterized the malignant melanoma lesion as atypical compound nevus with moderate atypia. Color-coded reference infrared (IR) images of the lesions and surrounding area (f—benign, g—malignant) recorded at ambient conditions are shown in the second row. No significant temperature difference is detected between the lesions and the surrounding healthy skin in these reference images. Local variations of skin temperature and properties cancel out in further analyses after subtracting the corresponding reference images (FIGS. 2F, 2G) from the measurement data acquired during the thermal recovery process.

Figures 2A, 2B, 2C, 2D, 2E, 2F, 2G, 2H, 2I, 2J, 2K:
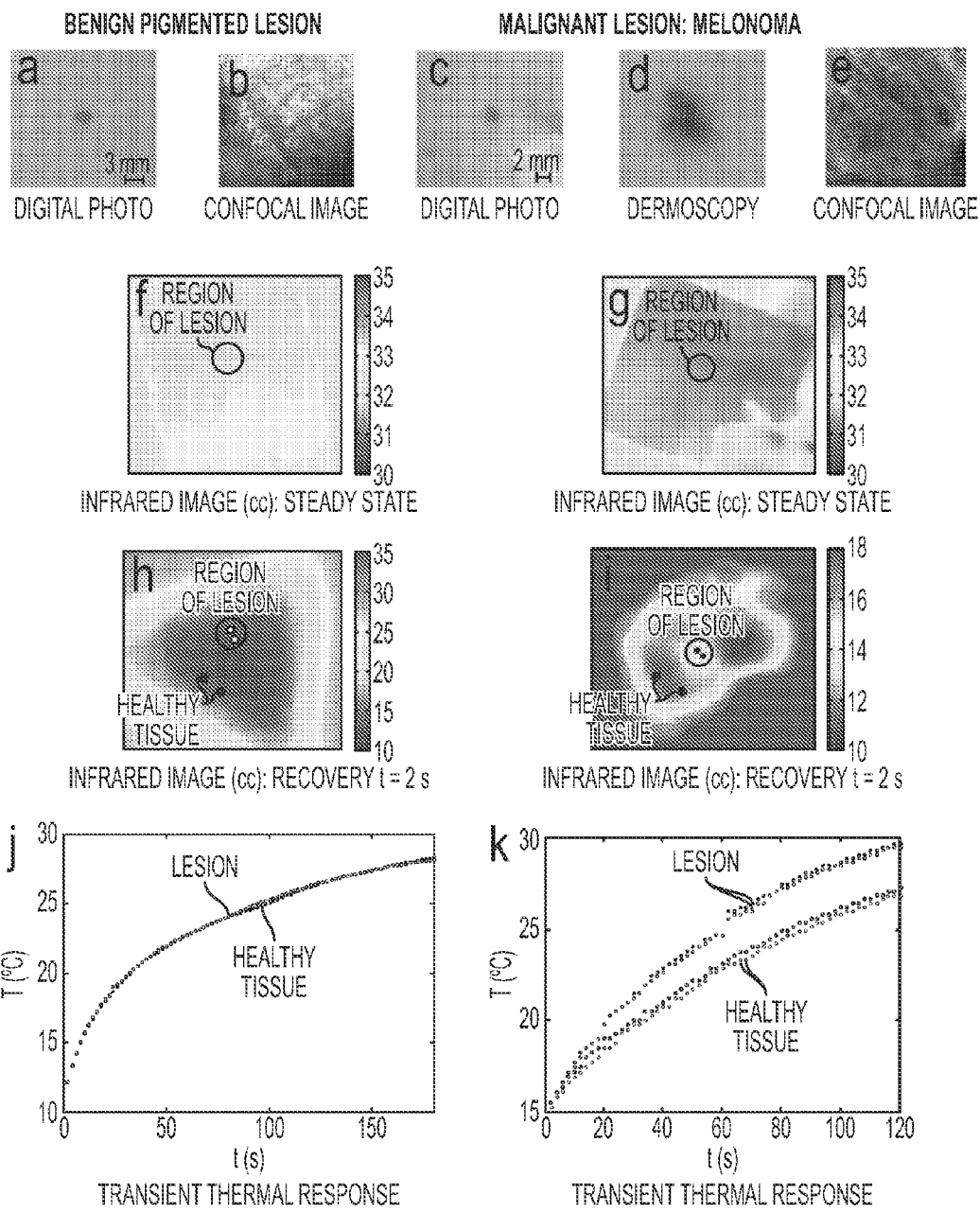
FIGS. 2A-2K are images obtained to illustrate some concepts of the current invention of a benign pigmented lesion (left) and a malignant melanoma lesion (right) using digital photography (a,c), confocal microscopy (b,e), dermoscopy (d) and infrared imaging (f-i) as well as diagrams of the measured thermal response as a function of time of the lesion and healthy tissue for the (j) benign case and (k) melanoma.

In our clinical trial, skin is cooled for 1 minute by applying a cold tissue to the area of the lesion (for images in FIGS. 2A-2K) or by blowing cold air. After removing the cooling excitation, the skin was allowed to reheat and return to ambient conditions and the thermal recovery process was recorded with the IR camera as a movie sequence. After appropriate processing and subtraction of reference image information, the temperature of the skin surface is accurately reconstructed at 2 seconds time intervals. The color-coded infrared images of the investigated regions 2 seconds into the thermal recovery are displayed in FIGS. 2H and 2I. The cold region in FIG. 2H is at uniform temperature at 2 s into thermal recovery: the lesion and the surrounding skin are at the same temperature (same color) indicating similar metabolic activity, which suggests that the lesion is benign. The results of the biopsy confirmed our conclusion reached using our imaging tool HRIS as well as the clinical assessment. On the other hand, the cold region (dark blue) in FIG. 2I displays a warmer circular region in the center of the cold region (light blue), at the location of the lesion, indicating increased metabolic activity and/or blood supply to the lesion, suggesting possible malignancy. The biopsy results confirmed that the lesion in the right-hand-side of FIG. 2 was a malignant melanoma lesion. In FIGS. 2J and 2K we compare the temperature at the center of the lesion and the temperature of the healthy skin away from the lesion as a function of time. As expected, the results in FIG. 2J do not show a temperature difference between the lesion and healthy skin. Temperature plots in FIG. 2K display significant temperature differences between healthy tissue and the lesion center during the thermal recovery (200 seconds). The magnitude of this temperature difference (FIG. 2K) as well as its time evolution are indicative of the metabolic activity level that could be potentially correlated with the malignant potential of the lesion. The results in FIG. 2 prove the hypothesis that the increased metabolic activity of the melanoma lesion can be detected by dynamic infrared imaging.

Figure 4:
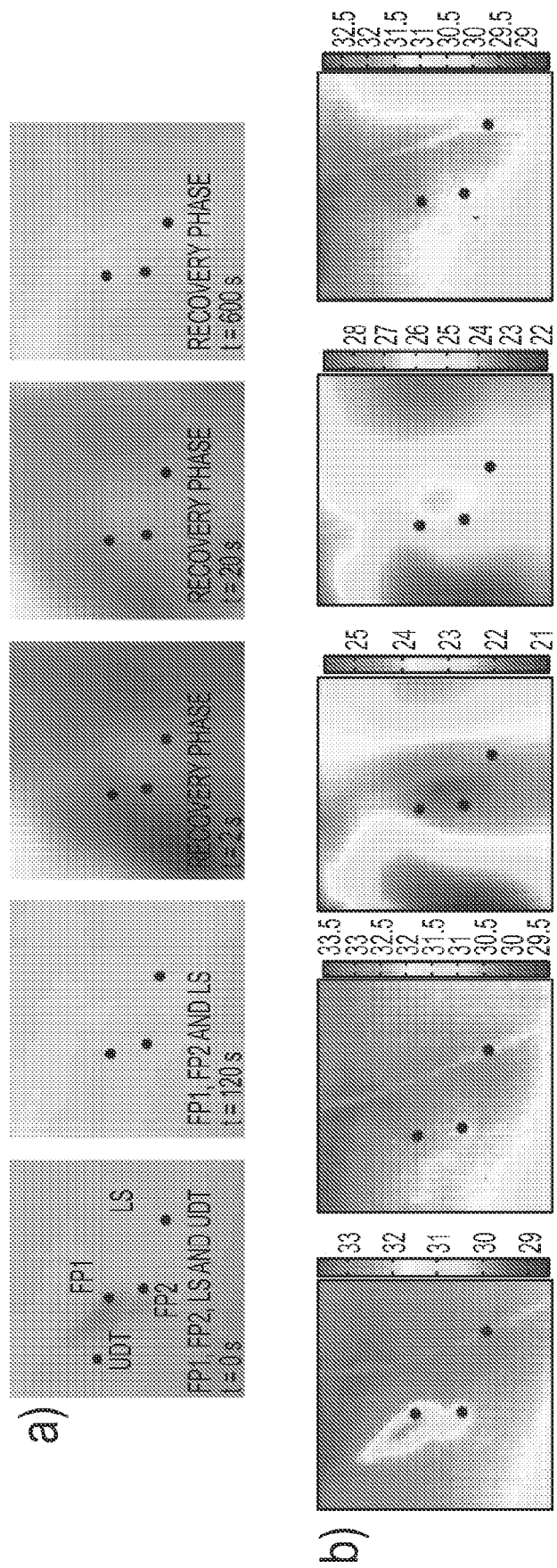
FIG. 4 shows infrared images to illustrate some concepts of the current invention.

In addition to the experiments in a clinical setting, infrared imaging experiments were conducted in a laboratory setting, first on the skin phantom and later on healthy human skin tissue. Sample infrared thermographic images of the skin recorded by M. Pirtini and C. Herman and subjected to a number of filtering operations to enhance the desired features and convert the grayscale information into color-coded temperature are displayed in FIG. 3. During the in vivo experiment with our imaging system, illustrated in FIG. 4, focal pressure was applied to healthy tissue at two locations, shown as points FP1 and FP2 in FIG. 4. Also a line scratch LS was applied to healthy tissue as shown in FIG. 4. Initially, FP1, FP2 and LS are clearly visible in the infrared image (first pair of greyscale-color images), however, they nearly disappear 120 s after application (second pair of greyscale-color images). At 120 s the cooling stress is applied for 3 minutes. The remaining three pairs of images show the skin during the thermal recovery phase after 2 s, 20 s and 600 s. From these images it is obvious that the cooling stress enhances the contrast between the FP1, FP2 and LS features and the undisturbed healthy tissue, and FP1, FP2 and LS again become visible in the infrared image.

A simplified computational model of skin tissue with a lesion was developed in the Heat Transfer Lab of JHU. Each layer of the skin tissue is modeled as a homogeneous medium of finite thickness h in the y direction and infinite dimensions in the x and z directions (FIG. 5). Each of these layers is characterized by a set of thermophysical properties, which were the subject of the sensitivity analysis. The bioheat equation describes the temperature distribution in each of the five tissue layers. Specifically, for regions n=1, 2, 3, 4, 5, the temperature is computed by solving the set of five coupled partial differential equations of the form $$\rho_n c_n \frac{\partial T_n}{\partial t} = k_n \nabla^2 T_n + \rho_b C_b w_b (T_b - T_n) + Q_n, h_{n-1} < y < h_n, h_0 = 0.$$

Figures 6A, 6B, 6C, 6D, 6E, 6F, 6G:
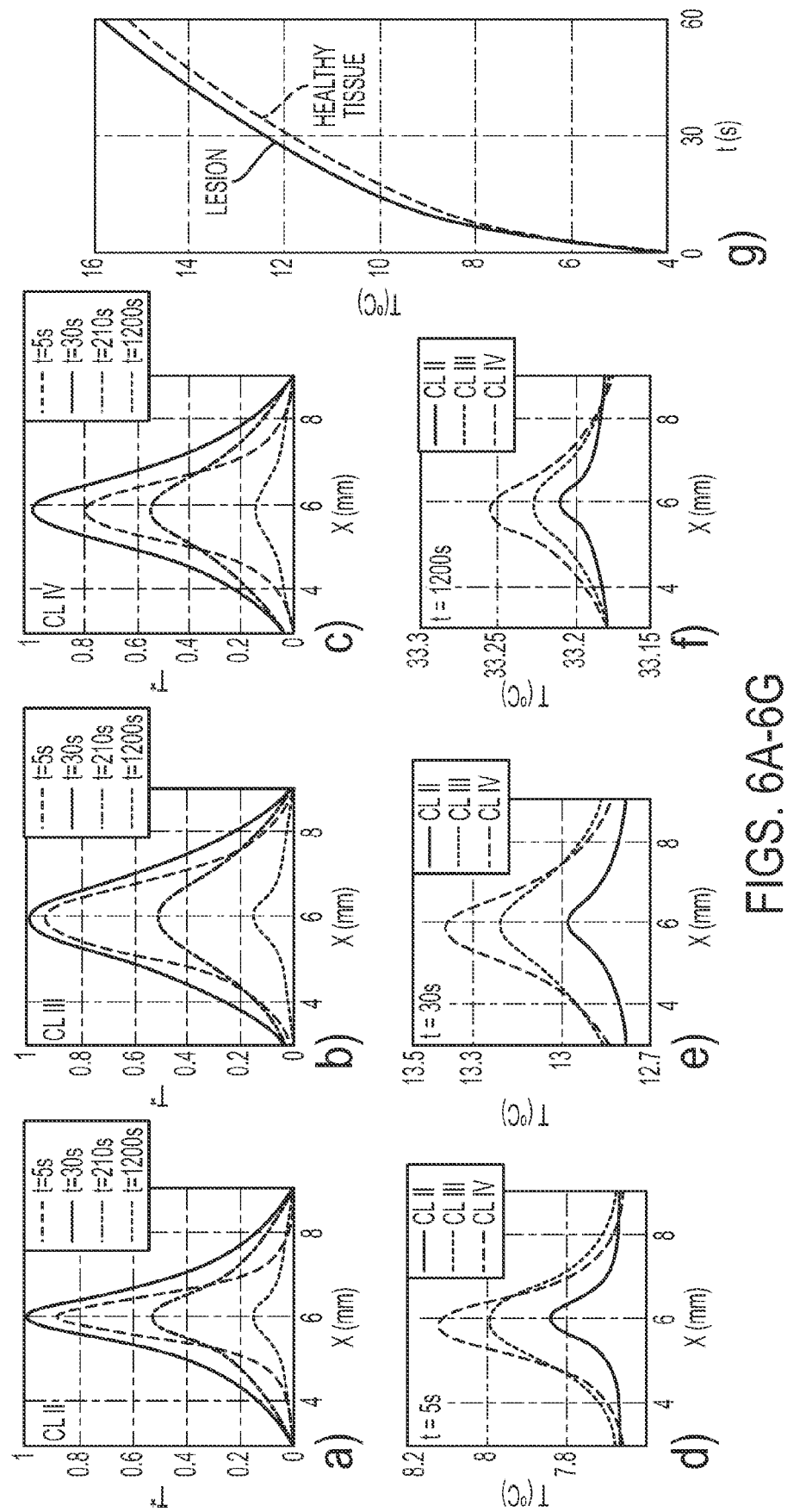
FIG. 6A-6G show computed dimensionless surface temperatures for selected recovery times a) Clark level II, b) Clark level III, c) Clark level IV; and surface temperature distributions of the three investigated Clark level lesions for recovery time d) t=5 s, e) t=30 s, f) t=1200 s; g) transient thermal response of lesion and healthy tissue as a function of time for (d-f), according to an embodiment of the current invention.

The commercial software COMSOL Multiphysics v3.4 (2008) was used in our analysis to solve the mathematical model. We considered very early stage melanoma, which are of particular interest in our study and represent the "worst case scenario". They are characterized by less than 2 mm invasion and no ulceration. We used the Clark level of invasion, which is determined by measuring of the depth of penetration of a melanoma into the skin. FIGS. 6A-6C display calculated nondimensional temperature (T*) at selected recovery times (5, 30, 210 and 1200 s) for each lesion invasion level characterized by Clark levels II-Iv. Earlier recovery times are selected for more detailed interpretation of surface temperature profiles in dimensional form for different Clark levels (FIGS. 6D-6F). The transient thermal response of the healthy skin tissue (3 mm away from the lesion) and the tissue immediately above the lesion are shown in FIG. 6G as a function of time. There is a distinct difference in the time evolution of the temperature in healthy tissue and the lesion.

3d Topographic Mapping of the Human Body

Accurate 3d topographic mapping of a specific human subject is of interest in numerous engineering and medical applications. Spatial accuracy is of primary concern in medical diagnostics. Some embodiments of the current invention provide a 3d imaging system that includes hardware and software to yield a 3d grid similar to that shown in FIG. 7. The hardware can include the equipment-supporting framework to accommodate white-light and IR imaging hardware, cameras and lenses, lighting arrangement and grid system (the shape and size of the grid pattern can be optimized). The framework can allow easy reconfiguring of the cameras in order to optimize the imaging system.

Software for camera calibration, image capture, image processing, including grid identification, model reconstruction from grid deformation, identification of the thermal markers and image tracking can be provided according to some embodiments of the current invention. The tracking of small movements of the subject and the thermal markers can be essential both in white-light and IR imaging in some applications. The cameras can be calibrated using a regular (cylindrical) object, for example.

For human shape reconstruction, the human body can be represented by a set of deformable superquadrics, which are generalized ellipsoids with global parameters controlling the global shape of the superquadric and local parameters to capture the fine information of the object surface. We can split the human body into parts, such as head, neck, shoulder, arms (upper, forearm), torso, pelvis, legs (thigh and calf) and feet, for example. The number of parts can be optimized to achieve the desired spatial resolution and each part can be represented by a deformable superquadric. A parametric representation can be defined with respect to the human-body-centered coordinate system and the human body parts can be identified by a set of key feature points. The information obtained in this way can be utilized to formulate a computational mesh (See, for example, http://freegamearts.tuxfamily.org/images/malebody_BETA1.png).

High-Resolution, High-Accuracy Transient Thermal Imaging

FIG. 1 is a schematic illustration of a thermal imaging system according to an embodiment of the current invention. The central piece of equipment used in the IR imaging is a Merlin midwave (3-5 μm) infrared camera (MWIR) that has a thermal sensitivity of 0.025° C., a 320×256 InSb focal plane array (FPA) and frame rate of 60 Hz. The camera is connected to a computer. Image acquisition software was developed to capture the movie sequences. The camera is calibrated in several steps as described in (Pirtini Cetingul and Herman 2009a,b, 2010), and the steps involve blackbody calibration, application of masks to account for the influence of ambient temperature, calibration for the actual subject, subtraction of the reference image from the measurement image sequence to eliminate the influence of local radiative property variations, etc.

In past studies the assumption was made that the surface area being imaged is relatively small, therefore the surface curvature could be neglected, and the camera axis was perpendicular to the skin surface. These assumptions no longer hold in full body imaging. 3d information on the subject is obtained from the white-light imaging system and thermal markers are used to match and align the white light and IR images. The number and location of the thermal markers used for an accurate IR reconstruction can be optimized for the particular application. For many applications, imaging accuracy with a resolution to allow detection of 1-2 mm diameter melanoma lesions, for example, will be used.

Modeling

We have previously developed a computational model for the dynamic thermal analysis of melanoma lesions. Our computational model, suitable for and intended for imaging of individual lesions, greatly oversimplifies the living system by assuming that the skin tissue is a semi-infinite medium (or layered flat structure) and the lesion is very small and located near the surface. Some embodiments of the current invention provide 3d temperature distributions on the skin surface as a function of time. Models according to some embodiments of the current invention can account for the entire human body and compute the thermal response of a larger lesion in the vicinity of a curved surface. The temperature distribution within the tissue and on the skin surface as a function of time can be computed for healthy and diseased tissue for different sizes and localizations of the tumor subjected to a cooling stress and subsequent thermal recovery.

A 3d full-body thermal model can couple a relatively crude thermal model of the body, such as the 16-cylinder-segment model (Kakuta et al. 2002), with the more comprehensive thermal model of skin tissue with and without embedded lesions (Pirtini Cetingul and Herman 2010). In the geometrical model of the human body each extremity segment can be represented by three concentric layers (bone, muscle and fat). The remaining segments, head, neck, thorax and abdomen, have an additional layer in the interior, corresponding to the organs. The results and data obtained as output of this model at the surfaces of the individual segments yields the boundary conditions for the more comprehensive thermal model of the skin. The 3d information can be incorporated into this model as well, by adjusting the thicknesses of the three external layers.

In addition to modeling data, we can also analyze this system as an inverse problem. Using tomographic reconstruction techniques we can reconstruct the lesion (dimensions and localization) from the surface temperature distribution and its time response for the types of excitation applied. It is well known that the accuracy of tomographic reconstruction increases when increasing the number of viewing directions/angles. We can take advantage of the dynamic response of the system (to different types of excitation) as well as prior knowledge of the properties and shape of the melanoma lesions to compensate for missing information in a spatial domain according to some embodiments of the current invention. We have developed a tomographic reconstruction code based on the ART (Algebraic reconstruction technique)—Sample method (Mewes, Herman, Renz, 1994) for the reconstruction of 3D temperature distributions from interferometric measurements. This code is available in the Heat Transfer Lab of JHU.

REFERENCES

1. Amalric, R. et al., 1975, La telethermographie dynamique en dermatologie, Ann. Dermatol. Syphiligr., vol. 102, 157-64.
2. Amalrich, R. et al., 1984, Value of infrared thermography in the assessment of malignant melanoma of the skin" In: Ring E F J, Phillips B, editors. Recent advances in medical thermography. New York/London: Plenum, vol. 62.
3. Anbar, M., 1998, Clinical thermal imaging today—shifting from phenomenological thermography to pathophysiologically based thermal imaging, IEEE Eng. Med. Biol. Mag., vol. 17 (4), 25-33.
4. Anbar, M., Graft, B. M., Hong, D., 1998, Thermology and facial telethermography. Part I: history and technical review, Dentomaxillofacial Radiology, vol. 27, 61-67, 1998.
5. Anbar, M., 2002, Assessment of physiologic and pathologic radiative heat dissipation using dynamic infrared imaging, Ann. NY Acad. Sci. 972, 111-118.
6. Andreassi, M., Andreassi, L., 2007, Utility and limits of noninvaisve methods in dermatology, Expert Rev. Dermatol., vol. 2, 249-255.9
7. Barnes, R. B., 1968, Diagnostic thermography, App. Opt., vol. 7 (9), 1673-1686.
8. Brasfield, R. D., Laughlia, J. S., Sherman, R. S., 1964, Thermography in the management of cancer: a preliminary report, Ann. NY. Aca. Sci., vol. 121, 235-247.
9. Brueschke, E., Haas, C., 1969, Image analysis of medical thermograms", Investigative Radiology, vol. 4, 28-35.
10. Bourjat, P., Gautherie, M., Grosshans, E., 1975, Diagnosis, follow-up and prognosis of malignant melanomas by thermography, Bibl. Radiol., (6), 115-127.
11. T. M. Buzug, S. Schumann, L. Pfa_mann, U. Reinhold, and J. Ruhlmann, 2006, Functional infrared imaging for skin-cancer screening", IEEE Eng. Med. Bio. Soc. Conf., 2766-2769.
12. Comsol Multiphysics 2008 Version 3.4 Comsol Inc.
13. Cristofolini, M., Piscioli, F., Valdagni, C., Della Selva, A., 1976, Correlations between thermography and morphology of primary cutaneous malignant melanomas", Acta. Thermogr., vol. 1, 3-11.
14. Cristofolini, M. et al., 1981, Uselessness of thermography for diagnosis and follow-up of cutaneous malignant melanomas", Tumori, vol. 67, 141-143.
15. Di Carlo, A., 1995, Thermography and the possibilities for its applications in clinical and experimental dermatology, Clin. Dermatology, vol. 13, 329-336.
16. Diakides, N. A., 1998, Infrared imaging: an emerging technology in medicine", IEEE Eng. Med. Bio., vol. 17, 17-18.
17. Godil, A., 2007, Advanced Human Body and Head Shape Representation and Analysis, Digital Human Modeling, HCII 2007, 92-100.
18. Gu, J., et al., 1998, A 3D Reconstruction System for Human Body Modeling, Lecture Notes In Computer Science; vol. 1537, 229-241.
19. Gulyaev, Y. V., Markov, A. G., Koreneva, L. G., Zakharov, P. V., 1995, Dynamical infrared thermography in humans, IEEE Eng. Med. Bio., vol. 14, 766-771.
20. Hartmann, M., Kunze, J., Friedel, S., 1981, Telethermography in the diagnostic and management of malignant melanomas", J. Dermatol. Surg. Oncol., vol. 7, 213-218.
21. Head, J. F., Wang, F., Lipari, C. A., Elliott, R. L., 2000, The important role of infrared imaging in breast cancer, IEEE Eng. Med. Biol. Mag., vol. 19, 52-57.

22. Helmy, A., Holdmann, M., Rizkalla, M., 2008, Application of thermography for noninvasive diagnosis of thyroid gland, IEEE Biomedical Eng., vol. 55 (3), 1168-1175.
23. Herman, C., Alani, R., Murphy, J., 2007, Transient Surface Temperature Response as Diagnostic Tool in Medicine and Engineering Applications. NSF Grant 0651981, Jul. 1, 2007-Jun. 30, 2010.
24. Herman, C., Alani, R. M., Pirtini Cetingul, M., 2009, High-resolution infrared imaging for enhanced detection, diagnosis, and treatment of cutaneous lesions, PCT International Application No. PCT/US2009/003319.
25. Hessler, C., Maillard, G. F., 1970, The contribution of thermography to the diagnosis and treatment of malignant melanoma", Schweiz. Med. Wschr., vol. 100(23), 972-975.
26. Hooshmand, H., Hashmi, M., Phillips, E. M., 2001, Infrared thermal imaging as a tool in pain management an 11 year study: I, Thermology International, vol. 11, 53-65.
27. Jiang, L. J. et al., 2005, A perspective on medical infrared imaging", J. Med. Eng. Tech., vol. 29 (6), 257-267.
28. Johns Hopkins Medical Institutions IRB, Mar. 30, 2009, protocol: NA_00016040, Using High Resolution Functional Infrared Imaging to Detect Melanoma and Dysplastic Nevi.
29. Jones, B. F., 1998, A reappraisal of the use of infrared thermal image analysis in medicine, IEEE Trans. Med. Imaging, vol. 17 (6), 1019-1027.
30. Jones. B. F., Plassmann, P., 2002, Digital infrared thermal imaging of human skin", IEEE Eng. Med. Bio., vol. 21, 41-48.
31. Keyserlingk, J. R., Ahlgren, P. D., Yu, E., Belliveau, N., Yassa, M., 2000, Functional infrared imaging of the breast, IEEE Eng. Med. Biol. Mag., vol. 19, 30-41.
32. Leong, I., et al., 2007, Automatic body feature extraction from a marker-less scanned human body, Computer-Aided Design, vol. 39, 568-582.
33. Luginbuhl, T., et al., 2009, A Model-Based approach for human body reconstruction from 3D scanned data, Lecture Notes In Computer Science, vol. 5496, 332-343.
34. Merla, A., Romani, G. L., Tangherlini, A., Romualdo, S. D., Proietti, M., Rosato, E., Aversa, A., Salsano, F., 2007, Penile cutaneous temperature in systemic sclerosis: a thermal imaging study, International Journal of Immunopathology and Pharmacology, vol. 20, 139-144.
35. Merla, A., et al., 2010, Thermal Imaging of Cutaneous Temperature Modifications in Runners During Graded Exercise, Ann. of Biomedical Eng., vol. 38 (1), 158-163.
36. Mewes, D., Herman, C., Renz, R., 1994, Tomographic measurement and reconstruction techniques, In Optical Measurements—Techniques and Applications, Editor: F. Mayinger, Springer Verlag, Berlin, 371-424.
37. Michel, U., Hornestein, O. P., Schonberger, A., 1985, Infrarotthermographie beim malignen melanom", Hautarzt, vol. 36, 83-89.
38. Ng, E. Y. K., Ung, L. N., Ng, F. C., 2001, Statistical analysis of healthy and malignant breast thermography, J. Med. Eng. Technol., vol. 25, 253-263.
39. Ng, E. Y. K, 2008, A review of thermography as promising non-invasive detection modality for breast tumor, International Journal of Thermal Sciences, vol. 48, 849-859.
40. Ng, E. Y. K., Acharya, U. R., 2008, A review of remote-sensing infrared thermography for indoor mass blind fever screening in containing an epidemic, IEEE Eng. Med. Bio. Mag., vol. 28, 76-83.
41. Nowakowski, A. Z., 2006, Advances of quantitative IR-thermal imaging in medical diagnostics, Proc. QIRT 2006.
42. Oliveira, F., et al., 2007, Infrared Imaging Analysis for Thermal Comfort Assessment, IEEE EMBS, 3373-3376.
43. Ortega, S. S., Garcia Vellado, J. V., 1982, Diagnostico termograpco del melanoma maligno, Actas Dermo-Sif., vol. 73, 89-94.
44. Patel, J. K., et al., 2008, Newer technologies/techniques and tools in the diagnosis of melanoma, Eur. J. Dermatol., vol. 18, 617-631.
45. Pirtini Cetingul, M., Herman, C., 2008, Identification of subsurface structures from the transient thermal response and surface temperature measurements, Proc. 5th European Thermal-Sciences Conf., May 18-22, 2008, Eindhoven, The Netherlands, ISBN 978-90-386-1274-4,
46. Pirtini Cetingul, M., Herman, C., 2009a, Identification of skin lesions from the transient thermal response using infrared imaging technique, IEEE 5th Int. Symp. on Biomedical Imaging: From Nano to Macro, May 14-17, 2008, Paris, France, vols. 1-4, 1219-1222.
47. Pirtini Cetingul, M., Herman, C., 2009b, Transient thermal response of skin tissue, Proc. ASME 2008 Summer Heat Transfer Conf., Aug. 10-14, 2008, Jacksonville, Fla., USA, ASME HT2008-56409, vol. 3, 355-361.
48. Pirtini Cetingul, M., Herman, C., Alani, R. M., 2009c, Skin imaging with infrared thermography and confocal microscopy, Proc. ASME 2009 Summer Heat Transfer Conf., Jul. 19-23, 2009, San Francisco, Calif., USA, ASME HT2009-88462.
49. Pirtini Cetingul, M. and Herman, C., 2010a, Heat transfer model of skin tissue for the detection of lesions: sensitivity analysis, Phys. Med. Biol., vol. 55, 5933-5951.
50. Pirtini Cetingul, M. Alani, R. M., and Herman, C., 2010b, Quantitative evaluation of skin lesions using transient thermal imaging, IHTC14-22465, Proceedings of the International Heat Transfer Conference, IHTC14, Aug. 8-13, 2010, Washington, D.C., USA.
51. Pirtini Cetingul, M. Alani, R. M., and Herman, C., 2010c, Detection of skin cancer using skin transient thermal imaging, SBC2010-19193, Proceedings of the ASME 2010 Summer Bioengineering Conference, SBC2010, Jun. 15-19, 2010, Naples, Fla., USA.
52. Pirtini Cetingul, M., 2010, Using high resolution infrared imaging to detect melanoma and dysplastic nevi, Ph.D. dissertation, Johns Hopkins University.
53. Psaty, E. L., Halpern, A. C., 2009, Current and emerging technologies in melanoma diagnosis: the state of the art", Clinics in Dermatology, vol. 27, 35-45.
54. Qi, H., Diakides, N. A., 2007, Infrared imaging in Medicine", CRC Press.
55. Ring, E. F. J., 1998, Progress in the measurement of human body temperature, IEEE Eng. Med. Bio. Mag., vol. 17, 19-24.
56. Ruddock, W., 2008, Advanced infrared resources, http://www.infraredthermography.com.
57. Stillwagon, G., Stillwagon, L. K., 1998, Vertebral subluxation correction and its affect on thermographic readings: a description of the advent of the visi-therm as applied to chiropractic patient assessment, J. of Vertebral Subluxation Research, vol. 2, 1-4.
58. Tapernoux, B., Hessler, C., 1977, Thermography of malignant melanomas", J. Dermatol. Surg. Oncol., vol. 3, 299-302.
59. Tan, J., Ng, E. Y. K., Acharya, U. R., Chee, C., 2009, Infrared thermography on ocular surface temperature: A review, Infrared Physics & Technology, 52, 97-108.

60. Vainer, G., 2005, FPA-based infrared thermography as applied to the study of cutaneous perspiration and stimulated vascular response in humans, Phys. Med. Biol., vol. 50, 63-94.
61. Vaviov, V. P., Vaviova, E. V., Popov, D. N., 2001, Statistical analysis of the human body temperature asymmetry as the basis for detecting pathologies by means of IR thermography, Thermosense XXIII, Proceedings of SPIE, vol. 4360, 482-491.
62. Wang, H., Wade, D. R., Kam, J., 2004a, IR imaging of blood circulation of patients with vascular disease, Proc. of SPIE 5405, 115-123.
63. Wang, S. Q., Rabinovitz, H., Kopf, M. W., Oliviero, M., 2004b, Current technologies for the in vivo diagnosis of cutaneous melanomas", Clin. Dermatology, vol. 22, 217-222.
64. Wang, C. L., 2005, Parameterization and parametric design of mannequins, Computer-Aided Design, vol. 37, 83-98.
65. Werghi, N., 2007, Segmentation and Modeling of Full Human Body Shape From 3-D Scan Data: A Survey, IEEE Transactions on Systems, Man, and Cybernetics—Part C: Applications and Reviews, vol. 37 (6), 1122-1134.

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

I claim:

1. A thermal imaging system, comprising:
   a data processing system;
   a geometrical scanning system constructed to communicate with said data processing system, said geometrical scanning system being adapted to scan at least a section of a surface of a subject under observation; and
   an infrared imaging system constructed to communicate with said data processing system, said infrared imaging system being adapted to image at least a portion of said section of said surface,
   wherein said data processing system is configured to receive data from said geometrical scanning system and to construct a surface map of said section of said surface of said subject under observation and to identify geometrical markers on said surface map based on said data from said geometrical scanning system,
   wherein said data processing system is configured to receive data from said infrared imaging system and to construct a thermal map of said portion of said section of said surface, to identify thermal markers on said thermal map based on said data from said infrared imaging system, and to register said thermal map to said surface map based on a correspondence between at least some of said geometrical and thermal markers, and
   wherein said data processor is configured to correct temperatures of said thermal map based on said surface map subsequent to said registering.

2. The thermal imaging system according to claim 1, wherein said geometrical scanning system and said thermal imaging system each have a resolution of at least 0.25 mm×0.25 mm.

3. The thermal imaging system according to claim 1, wherein said thermal imaging system has a temperature sensitivity of at least 0.025° K.

4. The thermal imaging system according to claim 1, further comprising a thermal stimulation system arranged to thermally stimulate at least a portion of said section of said surface of said subject under observation.

5. The thermal imaging system according to claim 4, wherein said data processing system is configured to receive data from said infrared imaging system at a plurality of times including at least one time prior to and at least one time subsequent to a thermal stimulation from said thermal stimulation system, said data processing system being configured to construct a plurality of thermal maps of said portion of said section of said surface corresponding to each of said plurality of times and to register each of said plurality of thermal maps to a corresponding surface map, and
   wherein said data processor is configured to correct temperatures of each of said plurality of thermal maps based on said corresponding surface map subsequent to said registering.

6. The thermal imaging system according to claim 5, wherein each surface map corresponding to each of said plurality of thermal maps is the same surface map.

7. The thermal imaging system according to claim 5, wherein at least one surface map corresponding to one of said plurality of thermal maps is corrected for motion of said subject.

8. The thermal imaging system according to claim 5, wherein said data processor is further configured to process said plurality of thermal maps to identify regions having abnormalities in thermal response.

9. The thermal imaging system according to claim 8, wherein said data processor is further configured to process said plurality of thermal maps using a thermodynamic model to identify regions having abnormalities in thermal response.

10. The thermal imaging system according to claim 9, wherein said thermodynamic model comprises a three-dimensional model of a section of said subject's body.

11. The thermal imaging system according to claim 9, wherein said thermodynamic model further comprises a thermodynamic model of melanoma.

12. The thermal imaging system according to claim 1, wherein said geometrical scanning system is adapted to scan one of a front or back half of said subject under observation, and said infrared imaging system is adapted to image one of a front or back half of said subject under observation to provide a half-body thermal imaging system.

13. The thermal imaging system according to claim 1, wherein said geometrical scanning system is adapted to scan substantially a full body of said subject under observation, and said infrared imaging system is adapted to image said substantially full body of said subject under observation to provide a full-body thermal imaging system.

14. A method of processing thermal imaging data, comprising:
   receiving data from a geometrical scanning system taken from a scan of at least a section of a surface of a subject under observation;
   receiving data from an infrared imaging system for at least a portion of said section of said surface;
   constructing a surface map of said section of said surface of said subject under observation and identifying geometrical markers on said surface map based on said data from said geometrical scanning system;
   constructing a thermal map of said portion of said section of said surface, identifying thermal markers on said thermal map based on said data from said infrared imaging system, and registering said thermal map to said surface map based on a correspondence between at least some of said geometrical and thermal markers; and correcting temperatures of said thermal map based on said surface map subsequent to said registering said thermal map to said surface map.

15. The method of processing thermal imaging data according to claim 14, further comprising receiving data from a thermal stimulation system arranged to thermally stimulate at least a portion of said section of said surface of said subject under observation.

16. The method of processing thermal imaging data according to claim 15, further comprising:
receiving data from said infrared imaging system at a plurality of times including at least one time prior to and at least one time subsequent to a thermal stimulation from said thermal stimulation system;
constructing a plurality of thermal maps of said portion of said section of said surface corresponding to each of said plurality of times;
registering each of said plurality of thermal maps to a corresponding surface map; and
correcting temperatures of each of said plurality of thermal maps based on said corresponding surface map subsequent to said registering.

17. The method of processing thermal imaging data according to claim 16, wherein each surface map corresponding to each of said plurality of thermal maps is the same surface map.

18. The method of processing thermal imaging data according to claim 16, wherein at least one surface map corresponding to one of said plurality of thermal maps is corrected for motion of said subject.

19. The method of processing thermal imaging data according to claim 16, further comprising processing said plurality of thermal maps to identify regions having abnormalities in thermal response.

20. The method of processing thermal imaging data according to claim 19, further comprising processing said plurality of thermal maps using a thermodynamic model to identify regions having abnormalities in thermal response.

21. The method of processing thermal imaging data according to claim 20, wherein said thermodynamic model comprises a three-dimensional model of a section of said subject's body.

22. The method of processing thermal imaging data according to claim 20, wherein said thermodynamic model further comprises a thermodynamic model of melanoma.

23. A non-transitory computer readable medium comprising software, which software, when executed by a computer, causes the computer to:
receive data from a geometrical scanning system taken from a scan of at least a section of a surface of a subject under observation;
receive data from an infrared imaging system for at least a portion of said section of said surface;

construct a surface map of said section of said surface of said subject under observation and identify geometrical markers on said surface map based on said data from said geometrical scanning system;
construct a thermal map of said portion of said section of said surface, identify thermal markers on said thermal map based on said data from said infrared imaging system, and register said thermal map to said surface map based on a correspondence between at least some of said geometrical and thermal markers; and
correct temperatures of said thermal map based on said surface map subsequent to said registering said thermal map to said surface map.

24. The computer readable medium according to claim 23, which software, when executed by a computer, further causes the computer to receive data from a thermal stimulation system arranged to thermally stimulate at least a portion of said section of said surface of said subject under observation.

25. The computer readable medium according to claim 24, which software, when executed by a computer, further causes the computer to:
receive data from said infrared imaging system at a plurality of times including at least one time prior to and at least one time subsequent to a thermal stimulation from said thermal stimulation system;
construct a plurality of thermal maps of said portion of said section of said surface corresponding to each of said plurality of times;
register each of said plurality of thermal maps to a corresponding surface map; and
correct temperatures of each of said plurality of thermal maps based on said corresponding surface map subsequent to said registering.

26. The computer readable medium according to claim 25, wherein each surface map corresponding to each of said plurality of thermal maps is the same surface map.

27. The computer readable medium according to claim 25, wherein at least one surface map corresponding to one of said plurality of thermal maps is corrected for motion of said subject.

28. The computer readable medium according to claim 25, which software, when executed by a computer, further causes the computer to process said plurality of thermal maps to identify regions having abnormalities in thermal response.

29. The computer readable medium according to claim 28, which software, when executed by a computer, further causes the computer to process said plurality of thermal maps using a thermodynamic model to identify regions having abnormalities in thermal response.

30. The computer readable medium according to claim 29, wherein said thermodynamic model comprises a three-dimensional model of a section of said subject's body.

31. The computer readable medium according to claim 29, wherein said thermodynamic model further comprises a thermodynamic model of melanoma.

* * * * *